United States Patent
McAffer et al.

(10) Patent No.: US 6,863,865 B2
(45) Date of Patent: Mar. 8, 2005

(54) STERILIZATION OF PHARMACEUTICALS

(75) Inventors: Ian G. C. McAffer, Biggin Hill (GB); Kailash S. Purohit, Des Plaines, IL (US)

(73) Assignee: Breath Limited (GB)

( * ) Notice: Subject to any disclaimer, the term of this patent is extended or adjusted under 35 U.S.C. 154(b) by 10 days.

(21) Appl. No.: 10/259,781

(22) Filed: Sep. 30, 2002

(65) Prior Publication Data
US 2003/0103864 A1 Jun. 5, 2003

Related U.S. Application Data

(63) Continuation of application No. PCT/GB01/05208, filed on Nov. 26, 2001.

(30) Foreign Application Priority Data

Nov. 24, 2000 (GB) ............................................. 0028763
May 14, 2001 (GB) ............................................. 0111745

(51) Int. Cl.[7] ............................ A61L 2/00; C07J 71/00; F28F 13/18; A23C 15/04; B01D 35/18
(52) U.S. Cl. ............................ 422/38; 422/21; 422/26; 422/109; 422/123; 422/307; 422/308; 422/309; 540/84; 540/85; 165/133; 165/158; 165/162; 165/163; 165/174; 99/483; 210/175; 210/766
(58) Field of Search ................................ 422/21–23, 26, 422/38, 109, 123, 307–309, 124–125, 305; 540/84–85; 165/158, 174, 133, 162, 163; 99/483; 210/175, 766

(56) References Cited

U.S. PATENT DOCUMENTS

| | | | |
|---|---|---|---|
| 4,695,454 A | | 9/1987 | Prince et al. ................. 424/89 |
| 5,603,894 A | * | 2/1997 | Aikus et al. ................... 422/23 |
| 5,636,317 A | | 6/1997 | Reznik ........................ 392/312 |
| 6,250,379 B1 | * | 6/2001 | Geissler et al. ............. 165/158 |
| 6,392,036 B1 | * | 5/2002 | Karlsson et al. .............. 540/63 |

FOREIGN PATENT DOCUMENTS

| | | | |
|---|---|---|---|
| EP | 0 571 771 A2 | 12/1993 | |
| EP | 0 722 075 A1 | 7/1996 | |
| WO | WO 96/13279 | * 5/1996 | ............. A61L/2/04 |
| WO | WO 99/25359 | 5/1999 | |
| WO | WO 99/32156 | 7/1999 | |
| WO | WO 99/61001 | 12/1999 | |
| WO | WO 00/57928 | 10/2000 | |

OTHER PUBLICATIONS

English language translation of EP 0 722 075, The British Library Nov. 10, 1999.

English language translation of EP 0 571 771, The British Library Oct. 4, 2000.

International Search Report for International Patent Application No. PCT/GB01/05208, mailed Mar. 1, 2002.

* cited by examiner

Primary Examiner—Elizabeth McKane
Assistant Examiner—Monzer R. Chorbaji
(74) Attorney, Agent, or Firm—Sterne, Kessler, Goldstein & Fox P.L.L.C.

(57) ABSTRACT

A method of sterilizing a pharmaceutical composition containing a suspension of a pharmaceutical comprises rapidly heating the pharmaceutical composition from ambient temperature to an elevated temperature, maintaining it at or above the elevated temperature for a period of time, and rapidly cooling the pharmaceutical composition to ambient temperature.

25 Claims, No Drawings

STERILIZATION OF PHARMACEUTICALS

The present invention concerns a method for the sterilization of drugs, in particular suspensions of drugs intended for use in nebulizers.

Previously it was acceptable for drugs intended for use in nebulizers to be prepared under "clean" conditions. Recently, however, the U.S. FDA has implemented a requirement for all nebulizer solutions to be sterile.

In the light of the U.S. FDA decision it is necessary to produce sterile suspension drugs in the U.S. This is emphasised by problems which have resulted from the use of "clean" suspensions. Multidose formulations made under "clean" conditions in which the composition was in a "preserved" state were previously acceptable in the U.S. However such preserved and clean-filled formulations have caused fatalities in the U.S. due to contamination.

A method of sterilizing dry, powdered budesonide is known from International Publication Number WO 99/25359. The method of sterilization requires budesonide powder to be sterilized and then be mixed with the other components of the formulation under sterile conditions. The drug formulation is subsequently made up under sterile conditions. This method does not permit the complete formulation to be sterilized immediately prior to dispensing into the final sterile vessel.

The sterilization of suspensions raises particular problems. The desired biological activity of the formulation commonly requires that the diameter of particles of the drug lies within a narrow range (typically less than 5 micrometers). The standard means of sterilization, that is the raising of the temperature of the formulation to 121° C. for 15 minutes, frequently destroys one or more of the components of the formulation. In addition this treatment results in the clumping or agglomeration of the drug particles in the suspension such that the efficacy of the resulting product is impaired or abolished.

Known alternative methods for the sterilization of pharmaceuticals are inappropriate for sterilizing suspension formulations of drugs. Pharmaceuticals may be sterilized by passage though a filter having a pore size of not more than 0.2 micrometers. However this cannot be used in the case of many suspensions as the required particle size in these formulations is significantly greater than this filter pore size. Similarly, pharmaceuticals may generally be sterilized by gamma-irradiation, but budesonide, for example, is destroyed by such treatment. No further methods for the sterilization of pharmaceuticals are currently acceptable to regulatory agencies.

An object of the present invention is to provide an alternative and/or an improved method for sterilization of suspensions of pharmaceuticals.

Accordingly, the present invention provides a method of sterilizing a pharmaceutical composition, which composition is or contains a suspension of a pharmaceutically active agent, comprising rapidly heating the pharmaceutical composition from ambient temperature to an elevated temperature, maintaining it at or above the elevated temperature for a period of time, and rapidly cooling the pharmaceutical composition to ambient temperature.

The heating process is carried out to achieve sterilization of the composition, while avoiding such excessive heating that unacceptable damage or deterioration to the composition occurs. A number of known pharmaceutically active agents are heat-sensitive, thus rendering them difficult to sterilize using hitherto known procedures. The present invention utilizes heat treatment that combines high temperature but short duration with the result that effective sterilization is obtained without adversely affecting the integrity or other physical characteristics of the active agent.

In a use of the invention, a suspension of a glucocorticosteroid, that is to say a suspension in water plus surfactant, in a liquid form, has been heated from room temperature to about 140° C., held around this temperature for 5 to 6 seconds and then rapidly cooled back to room temperature. Inspection of the suspension afterwards showed no apparent deterioration, and calculation of the kill rate, used to assess whether sterilization has been successful, confirmed a kill rate comfortably above 10, this value being regarded as the threshold for a sterilizing process.

The principle of high temperature short time treatment of liquids, in particular ultra high temperature processing of milk is described in particular in H. Burton, Ultra-High-Temperature Processing of Milk and Milk Products (Elsevier Applied Science Publishers Ltd 1988). In addition, there is a discussion of ultra high temperature sterilization of milk in Ullmann's Encyclopaedia, 5th edition, 1998 vol. A11, pages 549–552, and apparatus suitable for carrying out the high temperature short time processing methods used in the present invention is described therein.

The increase in temperature is preferably extremely rapid so that the composition is heated very quickly to a sterilizing temperature without spending unnecessary time at intermediate temperatures at which little or no sterilizing can occur but heat damage can. The step of increasing the temperature of the composition from the ambient temperature to the elevated temperature typically takes less than 10 seconds, less than 5 seconds, preferably less than 2 seconds.

Similarly, decreasing the temperature is also done rapidly for the same reasons, and typically the step of decreasing the temperature of the composition from the elevated temperature to ambient temperature takes less than 10 seconds, less than 5 seconds, preferably less than 2 seconds.

Good results have been seen by heating a suspension to the elevated temperature in around 1 second, and decreasing the temperature to ambient also in around 1 second.

The elevated temperature used in the method is sufficient to achieve sterilization before significant damage can be done to the composition. Suitable elevated temperatures are above about 130° C., more suitably above 135° C. and preferably at about or exceeding 140° C. In examples of the invention described below in more detail, good results have been obtained at temperatures of about 144 to 145° C. The ranges suitable may vary from one composition to the next and therefore the precise temperatures chosen can be adapted from the specific ranges mentioned while achieving the same result of sterilization without damaging the resulting composition.

In use of the invention, it is found that the kill rate of bacteria increases exponentially with temperature and while the rate of degradation of active ingredient in, say, a pharmaceutical that is being treated according to the invention is also increased with increase in temperature, the increase in degradation has a different, specifically a smaller, co-efficient. The method of the invention hence takes advantage of this by operating at a high temperature for a short period of time to achieve the bacteria kill necessary for sterilization but avoiding unacceptable damage to the chemical components of the composition.

Using a hold temperature of at or around 150° C. or higher produces exceptionally rapid bacteria kill, with little collateral damage to other components of a pharmaceutical composition, such as the active ingredient and its carrier. A rapid rise up to this temperature, in a period of about one or two seconds, can be achieved using pumps operating at speeds sufficiently fast to pump the liquid composition through heating pipes up to the desired hold temperature. However, if acceptable sterilization can be achieved at a lower hold temperature such as at or around 140° C., using pumps operating at a slower speed, and without cause of unacceptable damage to the pharmaceutical composition, then this balance of slightly lower temperature and slightly lower pump speed is generally preferable to excessively high pump speeds.

The duration of the elevated temperature step can also vary, and as described above the method is carried out to achieve a sterile end product without causing damage to the composition. Suitable durations are from about 2 to about 20 seconds, preferably from about 3 to about 10 seconds. These durations may also vary from one composition to the next. They may in addition vary according to the concentration of the particular components of the composition.

By reference to ambient temperature is generally meant reference to room temperature, in the range of about 15–25° C. However, reference to ambient temperature in terms of the temperature from which the composition being treated is raised to elevated temperature and to which the heated composition is cooled is intended to refer not to a specific temperature or specific range of temperatures but instead to any temperature at which the composition is substantially stable for long periods of time and is not adversely effected by being maintained at that temperature for a long period of time.

Pharmaceutical suspensions that can be sterilized according to the methods described herein are more or less without limit, though the method is particularly suitable for compositions including a drug in suspension, water or another solvent and, optionally, surfactants and/or preservatives.

The invention further provides a method of treating a pharmaceutical composition to reduce its microbial load, comprising rapidly heating the pharmaceutical composition from ambient temperature to an elevated temperature, maintaining it at or above the elevated temperature for a period of time, and rapidly cooling the pharmaceutical composition to ambient temperature. The method preferably comprises sterilization of the composition as described above.

In another aspect, the invention provides a method of sterilizing a concentrated formulation for use in a pharmaceutical composition, comprising rapidly heating the concentrated formulation from ambient temperature to an elevated temperature, maintaining it at or above the elevated temperature for a period of time, and rapidly cooling the concentrated formulation to ambient temperature. The sterilization is preferably carried out as described above.

Examples of concentrated formulations that can be sterilized include a pharmaceutical agent and a surfactant; a suspension of a drug in water or another solvent; a suspension of a drug in a surfactant solution. Once sterilized, these concentrates can be stored or used immediately or after an interval for preparation of formulations at the working concentration of the drug concerned.

A still further aspect of the invention lies in a method of sterilizing a pharmaceutical composition, characterized in that the sterilization is carried out by "square wave heating" and in that the sterilization is carried out continuously. The square wave heating suitably comprises rapidly heating the pharmaceutical composition from ambient temperature to an elevated temperature, maintaining it at or above the elevated temperature for a period of time, and rapidly cooling the pharmaceutical composition to ambient temperature.

The square wave heating treatment according to the invention preferably comprises an elevated hold temperature at which sterilization occurs but substantially no degradation of the composition occurs, and which temperature is generally in the range of 130° C. or more, preferably 135° C. and more preferably 140° C. or higher. The hold temperature is generally held for a period in excess of 1 and less than 20 seconds, more preferably in the range 2 to 10 seconds.

A particular advantage of this aspect of the invention is that the sterilization can be continuous and can be carried out in combination with other steps in preparation of the end product, such as particle size monitoring and adjustment, packaging, labelling, etc. For example, the method can further comprise dispensing sterilized pharmaceutical composition into storage vessels and sealing the storage vessels in a continuous process. The "blow-fill-seal" method is a packaging method that can be used in the invention, and typical storage vessels are selected from pre-sterilised ampoules, typically of plastic, metal or glass.

Where concentrates are sterilized, the method optionally includes diluting a sterile concentrate by a bulk composition under sterile conditions prior to dispensing into storage vessels.

Also provided in the invention are pharmaceutical compositions sterilized by the methods of the invention. Specifically, the invention provides a sterile suspension of a steroid obtainable by sterilizing a steroid suspension according to the invention, more particularly a sterile suspension of budesonide obtained by sterilizing a budesonide suspension according to the methods of the invention.

In a specific embodiment of the invention, a formulation comprising budesonide particles less than 5 $\mu$m in diameter, a polysorbate surfactant, water and preservatives which may include benzylkonium (bkc) and ascorbic acid has been sterilized by this method. Alternatively a concentrate of budesonide and polysorbate surfactant can be sterilized by this method prior to mixing with the remaining components of the complete formulation. Budesonide and other drugs that are formulated as suspensions can also be sterilized as a dispersion without surfactant present. Such treatment has been found not to result in the degradation of potentially heat-sensitive components of the formulation, and to enable production of sterilized suspensions having particles in a size range acceptable for pharmaceutical use.

Where a portion of the product of the invention has particles outside a given size range then it is optional to further process this product, for example to filter or otherwise remove particles of undesired size or to convert those particles into a desired size range. One way to carry out a particle size conversion is to use a micronizing device, conveniently as a component of the sterile production line, and a suitable device, referred to as a Microfluidizer®, is available from Microfluidics, Inc, described in WO 99/07466. Another way is to use a filter with a cut-off point to filter out particles in the suspension above a certain size. For inhalation purposes, a filter removing particles above about 10 $\mu$m may be used, for example.

The effectiveness of the treatment of the invention is unexpected as treatment at 140° C. would be expected to require minutes, not seconds, as the standard treatment requires 15 minutes at 121° C. to achieve sterility. Furthermore, such high temperatures would be expected to damage the formulation or drug substance. It is reported in WO 99/25359 (Astra) that long exposure of budesonide to high temperatures leads to agglomeration of the finely divided particles—the sterilization of budesonide is generally considered by the market to be impossible. Analysis of product of the invention has confirmed its chemical stability more than one month after sterilization.

This method of sterilization of pharmaceuticals may be applied to complete suspensions and to concentrates thereof. One application is the sterilization of asthma drugs. These may be sterilized by conventional terminal sterilization. However, the polymeric ampoules for such drugs must be able to be squeezed and such ampoules are not heat-resistant. Thus conventional blow-fill seal methods are not applicable in this context. The method of the invention allows such difficulties to be overcome.

The method of sterilization described has several advantages over previous methods of sterilizing pharmaceuticals. This method substantially does not damage the drug and allows the sterilization of a product for which this was previously believed not to be possible. The method removes the need to filter sterilize the bulk component of the formulation. Indeed, filter sterilization is not an absolute assurance of sterility as the integrity of the filter cannot be constantly monitored throughout the filling process. The use of high temperature/short time sterilization, therefore, can provide more effective sterilization than that resulting from filtration. The cost of this process may also be reduced by eliminating the requirement for expensive filters.

This method allows entire drug formulations or their component parts to be sterilized in line immediately prior to filling. The method is quick, and can be applied to an entire batch of formulation. In addition the method could be applied to the continuous production of a drug formulation. Further to this, high temperature/short time sterilization can be monitored throughout the filling process by validated thermocouple and flow rate recording to provide an absolute assurance of sterility. Analysis of products obtained in the specific embodiments have shown these to be sterile. Once sufficient data has been gathered for a given product, such monitoring allows batches of the product to be released for sale without waiting for the results of tests to confirm sterility. This reduces the cost and time delay presently incurred while awaiting the results of sterility release testing.

The invention is now illustrated in specific embodiments by way of the following examples and with reference to Table 1 which shows results of the sterilization method of the invention.

EXAMPLE 1

Preparation of a "Clean" Budesonide Formulation

Preparation of a clean suspension of budesonide particles for use in a nebulizer in which the final formulation comprises budesonide, a polysorbate surfactant, water and preservatives was carried out as follows.

A bulk solution consisting of all the components of the final formulation except budesonide and the surfactant was sterilized by passage through a 0.2 μm filter (0.1 μm is also suitable). The filtered solution was held at room temperature and a pressure of approximately 2 bar in a sterile vessel.

In the enclosed environment of a container cabinet, the polysorbate surfactant was filter sterilized into a sterile vessel. To this vessel micronized budesonide was added aseptically. The particle size of the budesonide was such that 100% of the particles were less than 10 μm and 95% of the particles were less than 5 μm in diameter. After addition the budesonide lay on top of the filtered polysorbate. Mixing was achieved by the use of a high shear mixing shaft. Twenty to twenty-five minutes of continuous mixing were required for the budesonide to go completely into suspension. After mixing was complete the mixing shaft was rinsed with sterile water and the vessel was sealed.

The complete formulation was produced by adding the budesonide/polysorbate concentrate to the bulk solution in a laminar flow hood after which the vessel was capped. A paddle at the bottom of this vessel rotating at approximately 700 rpm was required to maintain the suspension. The resulting formulation was dispensed to the final vessels under "clean" conditions.

This method results in a formulation that was "clean", but not sterile. The bioburden of the formulation was not increased during the process. The final bioburden of the formulation was required to be less than 10 CFU/100 ml.

EXAMPLE 2

Sterilization of a Budesonide Formulation

The formulation to be sterilized was passed through narrow lines of pharmaceutical quality stainless steel in which the sample was rapidly raised to an elevated temperature, maintained at this holding temperature for a period of time, then rapidly returned to ambient temperature. Parameters described in Table 1 are the BMRT (bulk mean retention time), that is the time between the sample being raised above ambient temperature and being returned to ambient temperature, and the FFERT, the time for which the sample is maintained at the elevated temperature. The BMRT always exceeds the FFERT by a small margin, hence the term square wave heating. The theoretical kill rate, Fo, may be calculated from the FFERT and the elevated temperature. The value of Fo is optimally greater than 10, but values greater than 8 are acceptable for the production of sterile formulations.

Ten liters of cleanly made budesonide solution, produced as in Example 1, was mixed in a bowl and four samples were run through the test rig. The data obtained showed that two sets of conditions resulted in values of Fo that were significantly greater than the required value of 10. Run 1 gave a Fo value of 19.9 with a temperature of 143.9° C. and a FFERT of 5.4 s. Run 4 gave an Fo of 24.1 with a hold temperature of 144.8° C. and a FFERT of 5.4 s. Runs 2 and 3 employed a lower hold temperature and did not give an acceptable value of Fo.

The results are shown in the following Table 1.

| Hold conditions analysis | Run 1 | Run 2 | Run 3 | Run 4 |
|---|---|---|---|---|
| Hold temperature ° C. | 143.9 | 133.0 | 139.4 | 144.8 |
| Hold time BMRT (seconds) | 7.5 | 9.4 | 6.9 | 7.5 |
| Hold time FFERT (seconds) | 5.4 | 6.7 | 4.5 | 5.4 |
| Legal Hold Fo (Kill factor) | 19.9 | 2.5 | 4.7 | 24.1 |

In addition to producing the required Fo, the conditions employed did not appear to alter the physical properties of the formulation.

EXAMPLE 3

Purity Testing of a Sterilized Budesonide Formulation

Chromatographic purity testing of budesonide suspension for nebulization, sterilized according to Example 2 was carried out to assess whether the treatment of Example 2 results in an increase of non-biological impurities in the samples. The proportions of budesonide-related compounds and unknown compounds in multiple samples from each test run of Example 2 were calculated, as was the % LC, a measure of degradation. In all cases, the values from the samples and the controls, which had not been subjected to the method of Example 2, were in significant agreement, both being less than 0.1%. This indicated that the process used for high temperature/short time sterilization did not result in an increase in the levels of impurities in the budesonide formulation.

EXAMPLE 4 (COMPARATIVE)

Attempt to Sterilize a Budesonide Suspension With High Intensity Light

An alternative method of sterilization of a budesonide suspension is treatment with high intensity light. The so-called "Pure-bright" process allows treatment with light at 900 times the intensity of sunlight at sea level. Attempts to sterilize budesonide formulations produced as in Example 1 resulted in the destruction of the budesonide. Although such a process might be expected to sterilize budesonide suspensions, the data clearly show that this method is not appropriate in that the drug is completely destroyed.

EXAMPLE 5

Evaluation of the Effect of High Temperature Short Time (HTST) Sterilization on Product Purity Using High Performance Liquid Chromatography Introduction This example was carried out to evaluate the effect of HTST on the chemical purity of pharmaceutical preparations by assessing the levels of degradation obtained in samples exposed to varying Fo (effective killing times) times. For the purposes of these experiments, budesonide suspensions were used in the evaluation.

Method

Budesonide suspensions were exposed to HTST at various flow rates and temperatures to achieve Fo times in the range 2.5 to 19.9. The samples were then evaluated using high performance liquid chromatography to assess the level of impurities present. The results obtained are presented in Table 2 below.

TABLE 2

Fo Exposure and Total Level of Impurities for HTST Treated and Control Budesonide Samples

| Sample Number | Fo (mins) | Total % Impurities |
|---|---|---|
| Sample B1 | Untreated | 0.70 |
| Sample B1 | 19.9 | 0.70 |
| Sample B2 | 2.5 | 0.78 |
| Sample B3 | 4.7 | 0.62 |
| Sample B4 | 24.1 | 0.73 |

Discussion and Conclusions

No HTST treated sample shows a significant increase in the total level of impurities present. This indicates that Fo exposures up to 24 will have no adverse effect on the chemical stability of budesonide. It is therefore likely that other compounds of similar or greater thermal stability will also be stable when exposed to similar Fo values.

EXAMPLE 6 (COMPARATIVE)

Evaluation of the Effect of Dry Heat and Autoclaving on the Impurity Content of Budesonide Introduction To produce a sterile suspension of budesonide the possibility of either terminal sterilization or sterilization of the active material prior to formulation needed to be considered. This example details the results of experiments undertaken to investigate three possible methods of achieving this.

Method

Experiment 1

To evaluate both the effects of dry heat and any potential benefits of autoclaving budesonide as a concentrated dispersion in polysorbate 80, samples of budesonide were treated with dry heat under standard atmospheric conditions at different temperatures for periods of 15 minutes. Subsequently the samples were dispersed in polysorbate 80 and autoclaved for 15 minutes at 121° C. A control sample was prepared by dispersing budesonide in polysorbate 80 and autoclaving at 121° C. for 15 minutes with no prior dry heating. This control sample was prepared to allow for the effect of the initial dry heating step to be evaluated.

Experiment 2

To evaluate the effect of terminal sterilization on the finished product, two suspensions of budesonide at 0.5 mg/mL were prepared in 4% polysorbate 80 solution. One sample was used as a control; the second was autoclaved at 121° C. for 15 minutes.

Results

The results obtained for experiments 1 and 2 are presented in Tables 3 and 4.

TABLE 3

Impurity Results Obtained for Experiment 1

| Sample Number | Sterilization Conditions | % Total Impurities |
|---|---|---|
| Control | Autoclave 121° C./15 minutes only | 1.19 |
| 1 | Oven 100° C./15 mins then autoclave 121° C./15 minutes | 2.76 |
| 2 | Oven 105° C./15 mins then autoclave 121° C./15 minutes | 3.19 |
| 3 | Oven 110° C./15 mins then autoclave 121° C./15 minutes | 4.64 |
| 4 | Oven 115° C./15 mins then autoclave 121° C./15 minutes | 3.13 |
| 5 | Oven 120° C./15 mins then autoclave 121° C./15 minutes | 3.64 |
| 6 | Oven 125° C./15 mins then autoclave 121° C./15 minutes | 4.25 |
| 7 | Oven 130° C./15 mins then autoclave 121° C./15 minutes | 4.57 |

TABLE 4

Impurity Results obtained for Experiment 2

| Sample Number | Sterilization Condition | % Total Impurities |
|---|---|---|
| Control | Not Applicable | 0.40 |
| 1 | Autoclave 121° C./15 mins | 6.87 |

Discussion

By comparing the results obtained for a standard autoclaved suspension of budesonide in polysorbate 80 with the results obtained for samples exposed to dry heat prior to autoclaving, it is evident that the dry heating process under atmospheric conditions increases the decomposition of budesonide. Hence, it is unlikely that sterilization under these conditions can be utilized. The results obtained for the sample autoclaved after dispersion in polysorbate 80 are better than those seen for the dispersion of budesonide in a 4% solution of polysorbate 80 as seen in Experiment 2. However, as there is still a trebling in the level of impurities present, this approach is still unlikely to be acceptable as a sterilization technique.

In experiment 2, the application of a standard autoclaving technique to budesonide suspension has also resulted in a significant increase in the levels of impurities present.

Conclusion

All three techniques for sterilization investigated resulted in unacceptable increases in the impurity levels present in budesonide suspensions. Hence, none of these methods are likely to be acceptable for the sterilization of budesonide.

EXAMPLE 7

High temperature short time sterilization of pharmaceutical samples

Introduction

Experiments were undertaken to demonstrate the ability of High Temperature Short Time (HTST) sterilization to kill micro-organisms in pharmaceutical samples. For the purposes of demonstrating the ability of this technique to sterilize such samples, the example of budesonide suspensions are below.

HTST Methodology

The methodology used to sterilize the samples is described above. The methods used to demonstrate sterility in this instance relate to the ability of the technique to achieve Fo times in excess of 6 and to reduce the total viable count of samples exposed to such Fo times to levels that indicate sterilization has taken place.

Samples

Two samples of budesonide suspension were prepared for evaluation. One sample was prepared with little care taken to protect the sample from contamination by micro-organisms present on equipment used for preparation or from the surrounding atmosphere (02401D). The other using good aseptic technique (02401E). Sample 02401D was prepared as a concentrated formulation comprising budesonide, polysorbate 80 and water, whereas 2401E was a fully formulated composition also comprising further excipients. The formulations of these samples are detailed in Table 5.

TABLE 5

Nominal Sample Concentration Evaluated in HTST Experiments

| Formulation Component | Sample 2401D | Sample 2401E |
|---|---|---|
| Budesonide Ph. Eur. | 1.31 mg/mL | 0.25 mg/mL |
| Polysorbate 80 Ph. Eur. | 10% w/v | 0.2 mg/mL |
| Citric Acid Ph. Eur. | — | 0.28 mg/mL |
| Sodium Citrate Ph. Eur. | — | 0.50 mg/mL |
| Sodium Chloride Ph. Eur. | — | 8.5 mg/mL |
| Disodium Edetate Ph. Eur. | — | 0.1 mg/mL |
| Water for injection Ph. Eur. | | To 1.0 mL |

Procedure for HTST Evaluation and Microbiological Testing

Each of the samples was passed through an HTST apparatus set up to allow sampling to occur at a number of points, each equating to a different hold time and Fo value. The early sampling points were not equipped for aseptic sampling. Hence, no microbiological evaluation was possible. However, terminal sampling (position C3) was undertaken aseptically in a class 100 laminar flow hood and these samples were sent for microbiological evaluation of the total viable count for bacteria and fungi. Table 6 shows the sampling points, temperatures and Fo values achieved for each of the evaluations.

TABLE 6A

Sampling Point, Temperature and Fo Times During HTST Experiment One

| Experiment Number | Sample Number | Sampling Point | Target Temperature ° C. | Fo |
|---|---|---|---|---|
| 1A | 02401D | C1 | 147.7 | 8 |
| 1B | 02401E | C1 | 147.7 | 8 |

Fo for C1 is based on an exposure time of 1.47 seconds

TABLE 6B

Sampling Point, Temperature and Fo Times During HIST Experiment Two

| Experiment Number | Sample Number | Sampling Point | Target Temperature ° C. | Fo |
|---|---|---|---|---|
| 2A | 02401D | C1 | 146.4 | 6 |
| 2B | 02401E | C1 | 146.4 | 6 |

Fo for C1 is based on an exposure time of 1.47 seconds

TABLE 6C

Sampling Point, Temperature and Fo Times During HTST Experiment Three

| Experiment Number | Sample Number | Sampling Point | Target Temperature ° C. | Fo |
|---|---|---|---|---|
| 3A | 02401D | C2 | 140.9 | 6 |
| 3A | 02401D | C3 | 140.9 | 8.8 |
| 3B | 02401E | C2 | 140.9 | 6 |

Fo for C2 is based on an exposure time of 6.01 seconds
Fo for C3 is based on an exposure time of 10.02 seconds

TABLE 6D

Sampling Point, Temperature and Fo Times During HTST Experiment Four

| Experiment Number | Sample Number | Sampling Point | Target Temperature ° C. | Fo |
|---|---|---|---|---|
| 4A | 02401D | C2 | 141.4 | 5.5 |
| 4A | 02401D | C3 | 141.4 | 8 |
| 4B | 02401E | C2 | 141.4 | 5.5 |
| 4B | 02401E | C3 | 141.4 | 8 |

Fo for C2 is based on an exposure time of 6.01 seconds
Fo for C3 is based on an exposure time of 10.02 seconds

TABLE 6E

Sampling Point, Temperature and Fo Times During HTST Experiment Five

| Experiment Number | Sample Number | Sampling Point | Target Temperature ° C. | Fo |
|---|---|---|---|---|
| 5A | 02401D | Bulk | — | — |
| 5A | 02401D | C2 | 140.1 | 4.1 |
| 5A* | 02401D | C3 | 140.1 | 6.0 |
| 5B | 02401E | Bulk | — | — |
| 5B | 02401E | C2 | 140.1 | 4.1 |
| 5B* | 02401E | C3 | 140.1 | 6.0 |

Fo for C2 is based on an exposure time of 6.01 seconds
Fo for C3 is based on an exposure time of 10.02 seconds
Note:
Samples marked with asterisk (*) were used to evaluate total viable count (TVC) before and after HTST treatment.

Microbiological Evaluation

The Samples annotated in Table 6E were evaluated for microbiological bioburden both before and after HTST treatment. The level of microbiological contamination was evaluated using standard methods of (BP) appendix XIV B; part 1 of the evaluation was a specified micro-organisms test and part 2 was an evaluation of total viable count (TVC). The results obtained are detailed in Table 7.

TABLE 7

Microbiological Bioburden Before and After HTST Treatment

| Batch Number | Sampling Point | Fo | Bacteria | Fungi |
|---|---|---|---|---|
| 02401D | Bulk Sample | N/A | 8150000 | <1 |
| 02401D | Exp. 5A C3 | 6.0 | <1 | <1 |
| 02401E | Bulk Sample | N/A | <1 | <1 |
| 02401E | Exp. 5B C3 | 6.0 | <1 | <1 |

Exp. = Experiment

Discussion and Conclusions

The results obtained during these experiments prove that on a practical basis it is possible to vary the Fo times for a pharmaceutical material in suspension by varying the hold times and temperatures to which samples are exposed. Furthermore, it has also been demonstrated that the technique of HTST is capable of making substantial reductions in the level of micro-organisms present in a pharmaceutical material to leave a product that is free of microbial contamination.

The invention thus provides methods for sterilization of pharmaceutical compositions.

What is claimed is:

1. A method of sterilizing a pharmaceutical composition, comprising rapidly heating the pharmaceutical composition from ambient temperature to an elevated temperature, maintaining it at or above the elevated temperature for a period of time, and rapidly cooling the pharmaceutical composition to ambient temperature, wherein the pharmaceutical composition is or contains a suspension of a glucocorticosteroid.

2. The method of claim 1, comprising increasing the temperature of the composition from the ambient temperature to the elevated temperature in less than 5 seconds.

3. The method of claim 1, comprising decreasing the temperature of the composition from the elevated temperature to ambient temperature in less than 5 seconds.

4. The method of claim 1, comprising heating the composition to an elevated temperature exceeding 130° C.

5. The method of claim 1, wherein the period of time is less than 20 seconds and greater than 2 seconds.

6. The method of claim 1, wherein the pharmaceutical composition comprises a drug in suspension, water or another solvent and, optionally, surfactants and/or preservatives.

7. The method of claim 6 wherein the composition is a budesonide suspension.

8. The method of claim 1, wherein said glucocorticosteroid is not degraded during the sterilization.

9. A method of treating a pharmaceutical composition to reduce its microbial load, comprising rapidly heating the pharmaceutical composition from ambient temperature to an elevated temperature, maintaining it at or above the elevated temperature for a period of time, and rapidly cooling the pharmaceutical composition to ambient temperature, wherein the pharmaceutical composition comprises a glucocorticosteroid in suspension.

10. The method of claim 9, comprising maintaining the composition at or above the elevated temperature for a time necessary for sterilization to be achieved.

11. The method of claim 9, wherein said glucocorticosteroid is not degraded during the treatment.

12. A method of sterilizing a concentrated formulation for use in a pharmaceutical composition, comprising rapidly heating the concentrated formulation from ambient temperature to an elevated temperature, maintaining it at or above the elevated temperature for a period of time, and rapidly cooling the concentrated formulation to ambient temperature, wherein the concentrated formulation is or contains a suspension of a glucocorticosteroid.

13. The method of claim 12, comprising increasing the temperature of the composition from the ambient temperature to the elevated temperature in less than 5 seconds.

14. The method of claim 12, comprising decreasing the temperature of the composition from the elevated temperature to ambient temperature in less than 5 seconds.

15. The method of claim 12, comprising heating the composition to an elevated temperature exceeding 130° C.

16. The method of claim 12, wherein the period of time is less than 20 seconds and greater than 2 seconds.

17. The method of claim 12, wherein the concentrated formulation is selected from a glucocorticosteroid and a surfactant;

a suspension of a glucocorticosteroid in a surfactant solution; and a suspension of a glucocorticosteroid in water or another solvent.

18. The method of claim 12, wherein said glucocorticosteroid is not degraded during the sterilization.

19. A method of sterilizing a pharmaceutical composition, comprising:

carrying out the sterilization by "square wave heating," and carrying out the sterilization continuously, wherein the composition comprises a glucocorticosteroid in suspension.

20. The method of claim 19, wherein square wave heating comprises rapidly heating the pharmaceutical composition from ambient temperature to an elevated temperature, maintaining it at or above the elevated temperature for a period of time, and rapidly cooling the pharmaceutical composition to ambient temperature.

21. The method of claim 19, further comprising dispensing sterilized pharmaceutical composition into storage vessels and sealing the storage vessels in a continuous process.

22. The method of claim 21 wherein dispensing is by the "blow-fill-seal" method.

23. The method of claim 21, wherein the storage vessels are selected from pre-sterilized ampoules, of polymeric material, metal or glass.

24. The method of claim 21, optionally comprising diluting a sterile concentrate by a bulk composition under sterile conditions prior to dispensing into storage vessels.

25. The method of claim 17, wherein said glucocorticosteroid is not degraded during the sterilization.

* * * * *